US00PP16284P2

(12) United States Plant Patent
Ramming et al.

(10) Patent No.: US PP16,284 P2
(45) Date of Patent: Feb. 21, 2006

(54) GRAPEVINE DENOMINATED 'AUTUMN KING'

(50) Latin Name: *Vitis vinifera L.*
Varietal Denomination: Autumn King

(75) Inventors: David W. Ramming, Fresno, CA (US); Ronald E. Tarailo, Fresno, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 161 days.

(21) Appl. No.: 10/953,387

(22) Filed: Sep. 28, 2004

(51) Int. Cl.
*A01H 5/00* (2006.01)

(52) U.S. Cl. ..... Plt./207
(58) Field of Classification Search ..... Plt./207
See application file for complete search history.

(56) References Cited

PUBLICATIONS

Bryant, D. New table grapes presented. Western Farm Press, Mar. 17, 2001 [retrieved on Apr. 21, 2005]. Retrieved from the Internet: <http://westernfarm press.com/mag/arming_new_table_grapes/>.*

Ramming, D., "USDA Grape Breeding Program and Promising Experimental Selections," San Joaquin Valley Table Grape Seminar, Feb. 21, 2001 Visalia, CA.

Ramming, D. et al., "Development of Seedless Grapes for the Fresh Market Including Types Resistance to Powdery Mildew—2000," 2000–01 Viticulture Research Report, California Table Grape Commission (2000) vol. XXIX.

Ramming, D., et al. "Development of Seedless Grapes for the Fresh Market Incuding Types Resistance to Powdery Mildew—2001," 2001–02 Viticulture Research Report, California Table Grape Commission (2001) vol. XXX.

Ramming, D. et al., "Development of Seedless Grapes for the Fresh Market Including Types Resistance to Powdery Mildew—2002," 2002–03 Viticulture Research Report, California Table Grape Commission (2002) vol. XXXI.

Ramming, D. et al., "Development of Seedless Grapes for the Fresh Market Including Types Resistance to Powdery Mildew—2003," 2003–04 Viticulture Research Report, California Table Grape Commission (2003) vol. XXXII.

* cited by examiner

*Primary Examiner*—Anne Marie Grunberg
*Assistant Examiner*—June Hwu
(74) *Attorney, Agent, or Firm*—Margaret A. Connor; John D. Fado; Leslie Shaw

(57) ABSTRACT

A new and distinct variety of grapevine denominated 'Autumn King' which is characterized by its late season ripening seedless fruit, attractive pale green coloration, its cylindrical to ovoid fruit shape, its firm fruit texture with neutral sweet flavor, and its medium to tight cluster.

2 Drawing Sheets

BACKGROUND OF THE INVENTION

The present invention relates to a new and distinct variety of grapevine, *Vitis vinifera* L., which will hereinafter be denominated varietally as the 'Autumn King' grapevine, and, more particularly, to a grapevine which has fruit maturing for commercial harvesting and shipment approximately October 23 in the San Joaquin Valley of central California. The fruit has an attractive pale green skin coloration at maturity with large cylindrical to ovoid shape seedless berries.

The grapevine of the present invention originated from a hand-pollinated cross of United States Department of Agriculture selection 'A61-20' (unpatented) and the United States Department of Agriculture selection 'B99-131' (unpatented) made in 1993 at the United States Department of Agriculture, Agricultural Research Service, Postharvest Quality and Genetics Research Unit plots at California State University, Fresno, in Fresno Calif. The female was 'A61-20', a seeded white-fruited grapevine having large size, ovoid berries with firm flesh and good skin, and a neutral flavor. The fruit of the 'A61-20' ripen about two weeks before the instant variety. The pollen parent was 'B99-131', a seedless white fruited grape with very large size, oval berries with medium skin and medium firm flesh. The fruit of the 'B99-131' grapevine ripen one month before the variety of the subject invention. Both of the parents of the instant cultivar are hybrids of the grapevine genus and species *Vitis vinifera* L.

The seeds resulting from this controlled hybridization were germinated in the greenhouse during the winter and spring of 1994. The resulting seedling population totaled 534 individual plants. All seedlings were planted in the spring of 1994 in a vineyard at the United States Department of Agriculture, Agricultural Research Service plots on the California State University, Fresno, campus in Fresno, Calif. The seedlings fruited in the summer of 1996 and one, the grapevine of the present invention, was designated as 'C67-120' and selected for its attractive pale green seedless, medium firm, large berry size, good fruit quality and late maturity.

In 1997 at the inventors' direction, the grapevine of the subject invention was propagated asexually by rooting hardwood cuttings at Fresno, Calif. and a test planting of two grapevines of the subject invention was established in the United States Department of Agriculture, Agricultural Research Service plots on the California State University, Fresno campus. Subsequently in 1998 a larger test planting of 24 vines was established with rooted hardwood cuttings of the instant invention. The instant cultivar rooted readily from hardwood cuttings. All grapevines of the new variety planted from hardwood cutting propagation, fruited in the third season of growth after planting. All propagules, or resulting plants, of the present invention have been observed by the inventors to be true to type in that all asexual reproduced grapevines of the variety possessed the characteristics identical to those of the original parent grapevine.

SUMMARY OF THE INVENTION

The grapevines of the subject invention possess medium vigor and have produced fruit as own-rooted grapevines. The size of the grapevines was determined by growing the grapevines on a three cross arm 'T' type trellis structure with a top cross arm of 122 cm in length set 189 cm above the ground; a second cross arm of 102 cm in length set 156 cm above the ground; and a third cross arm 91 cm in length set 125 cm above the ground. The trellis structure had two wires per cross arm and indicted a grapevine height of 200 cm and a grapevine spread of 199 cm.

The fruit of the new variety ripens late, about 8 weeks after the 'Thompson Seedless' (non-patented) and 4 weeks after 'Autumn Seedless' (non-patented). The average ripening date in Fresno, Calif. is October 23. Berries adhere medium well to the fruit pedicel and have minimal shatter from the clusters during storage. The fruit is pale green in color at maturity. The fruit shape is cylindrical to ovoid. Fruit skins are medium thick and similar to the 'Thompson Seedless' grapevine. 'Autumn King' differs from 'Thompson Seedless', ripening 8 weeks later. The pulp of the fruit adheres to the skins of the berry and the fruit texture is firm and meaty. The berries are large to very large in size, or 9.8 grams. The flavor of the fruit is sweet and has been rated good. Soluble solids concentration of the juice at fruit maturity averages 18.6% with titratable acid of 0.31 grams/100 milliliters of juice. The fruit is of the stenospermocarpic type of seedlessness and contains small, aborted seed traces that are not noticeable when eaten. The fruit clusters are usually borne on the average of 1.02 per shoot on cane pruned vines. The fruit clusters are conical and are medium in size, or 539 grams, medium to slightly tight and attractive. The fruit cluster peduncles are medium in length.

The grapevine and fruit of the new variety are susceptible to powdery mildew disease of grape plants. A spray program for powdery mildew disease control is required.

BRIEF DESCRIPTION OF THE DRAWINGS

The drawings of the grapevine of the present invention are color photographs showing in FIG. 1 a typical specimen of the fruit and in FIG. 2 a shoot with leaves and a flower cluster all of the new variety of the present invention.

The color of the phtographs is as nearly true as it is reasonably possible to provide in such color photographs. Description of the new invention applies to vines of 'Autumn King' grown on its own roots at a density of 1,119 vines per hectare in Fresno County, Calif. in 2002. These vines were in their second year of full production having been planted in 1998.

DETAILED BOTANICAL DESCRIPTION

Figure 1:
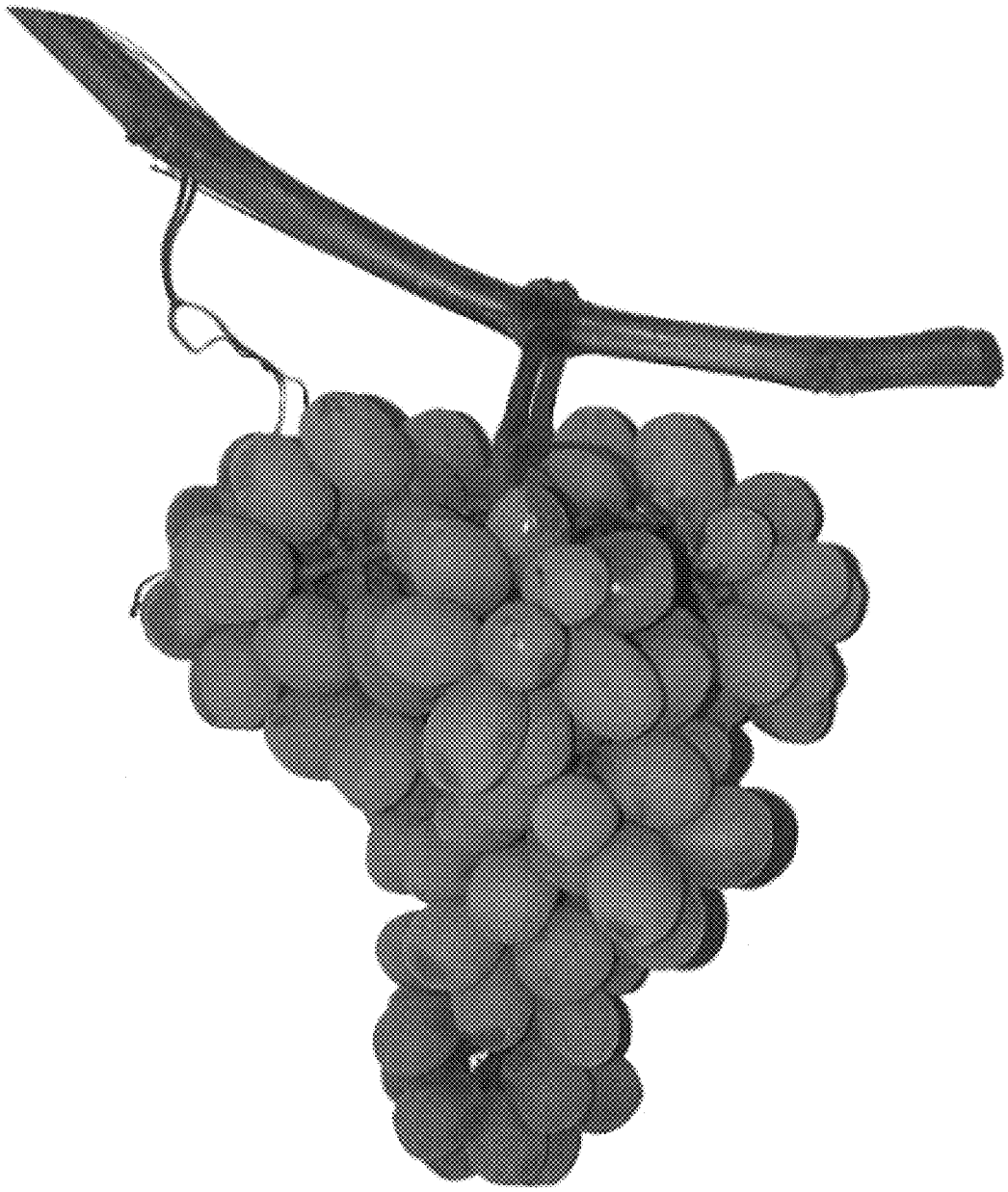
Figure 2:
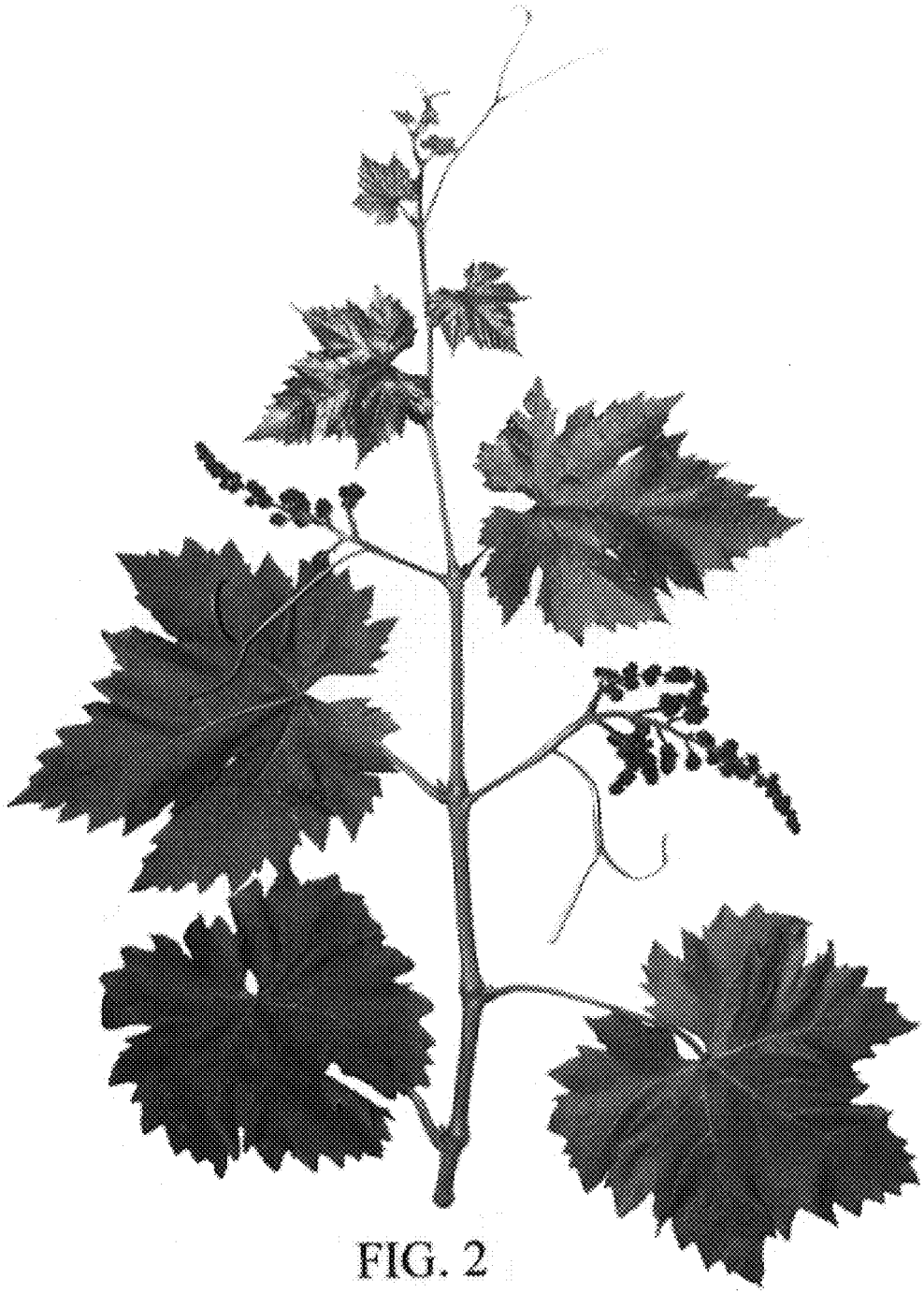

The new variety cv. 'Autumn King' may be distinguished from other commercial grape cultivars known to us by a combination of characteristics, including its late season ripening seedless fruit with attractive pale green coloration, its medium firm fruit texture with a neutral sweet flavor, its cylindrical to ovoid fruit shape and its medium to tight cluster.

The new variety of grapevine is most similar to its pollen parent 'B99-131' by having similar berry size and pale green fruit. It is distinguished therefrom and an improvement thereon in a number of fruit characteristics. The flesh of the new variety is firmer, the skin color is more attractive not showing veins. The berry shape is cylindrical to ovoid compared to the oval to round berries of 'B99-131'. The most distinguishing difference is the maturity time, being 4 weeks later thatn the pollen parent. The new grapevine is also similar to the commercial varieties 'Thompson Seedless' and 'Autumn Seedless' in that they have pale green seedless neutral flavored fruit. It is distinguished therefrom and an improvement thereon in that the berries of tne new variety are larger that those of 'Thompson Seedless' and 'Autumn Seedless'. It is also distinguished from 'Thompson Seedless' and 'Autumn Seedless' by ripening 8 and 4 weeks later, respectively.

The new variety also differs substantially from its mother parent 'A61-20'. It is distinguished therefrom and an improvement thereon in that the new variety is seedless, having small aborted (stenospermocarpic) seeds, while 'A61-20' is seeded with functional seeds. The berries of the new variety are substantially larger, being on average about 9.8 grams, while the berries of 'A61-20' are about 6.8 grams.

Referring more specifically to the botanical details of this new and distinct variety of grapevine, the following has been observed under the ecological conditions prevailing at the orchard or origin which is located in Fresno in the San Joaquin Valley of central California. All major color code designations are by reference to the *Dictionary of Color*, by Maerz and Paul, First Edition, 1930. Common color names are also occasionally employed. Where dimensions, sizes, colors and other characteristics are given, it is to be understood that such characteristics are approximations of averages set forth as accurately as practicable. The description hereof was taken from specimens grown in Fresno, Calif. The grapevines used for measurement were grown in a fine sandy loam soil and the grapevines were irrigated using trickle, or drip irrigation. In a substantial part, the data hereof was from grapevines that were five (5) years old.

VINE

Generally:

*Size.*—Medium. Grapevine size as determined on grapevines growing on a three cross arm 'T' trellis with the top cross arm 122 cm long set 189 cm above the ground; the second cross arm 102 cm long set 156 cm above the ground; and the third cross arm 91 cm long set 125 cm above the ground. There were two wires per cross arm and was trained to produce a grapevine height of 200 cm and a grapevine spread of 199 cm.

*Vigor.*—Medium vigor. Vigor as measured by weighing prunings at dormant pruning for cane pruned grapevines (with 6 canes and an average of 15 buds per cane) was 4.5 Kg.

*Productivity.*—Productive, 18.5 Kg per grapevine on grapevines spaced 8 ft. (243.84 cm) by 12 ft. (365.76 cm).

*Regularity of bearing.*—Regular. Annual pruning of canes is required for reliable production.

CANES

*Size.*—Diameter — Mature Canes — Medium diameter, medium vigor, upright in growth habit.

*Mature canes.*—Diameter — Internode Base — 11.8 mm.

*Mature canes.*—Diameter — Internode Midpoint — 9.5 mm.
*Mature canes.*—Diameter — Internode Tip — 4.2 mm.
*Mature canes.*—Diameter — Node Base — 13.4 mm.
*Mature canes.*—Diameter — Node Midpoint — 11.6 mm.
*Mature canes.*—Diameter — Node Tip — 5.5 mm.
*Internode length.*—Base — 5.9 cm.
*Internode length.*—Midpoint — 7.4 cm.
*Internode length.*—Tip — 4.1 cm.
*Average length of canes.*—263.3 cm.
*Surface texture.*—Smooth.
*Color of mature cane.*—Brown (plate 14 D8). No anthocyanin observed on mature canes.
*Buds.*—Color — Brown (plate 15 A10).
*Buds.*—Texture — Smooth.
*Dormant bud* (*compound bud or eye*).—Width — At base of cane 5.3 mm; at midpoint of cane 6.6 mm and at tip of cane 4.1 mm. The average number of buds on a current, single-season growth cane is 44.
*Date of bud break.*—March 29, late season.
*Young shoots.*—Young shoots have cobwebby indument.
*Diameter of young shoots in spring* (*measured when shoots are 24 inches*).—At base 8.3 mm, at midpoint 5.8 mm and at tip 2.8 mm.
*Internode length.*—7.2 cm at $4^{th}$ internode from base.
*Young shoots.*—Color — Light yellow green (plate 20 J6) with slight bronze on edge.
*Stem of shoot tip.*—Color — Yellow green (plate 20 K7) with occasional red on the sun exposed side.
*Shoot.*—Shape — Straight.
*Shoot tip.*—Form — Open.
*Tendrils.*—Size — Length — 18.6 cm.
*Tendrils.*—Size — Diameter — 2.21 mm.
*Tendrils.*—Shape — Usually biforcated or triforcated and curled on distal end.
*Tendrils.*—Pattern — Found beginning opposite node 8, then again at nodes 10, 11, 13, 14, 16, 17 with this repeating intermittent pattern to the distal end of the cane.
*Tendril.*—Color Immature Growth — Yellow green (plate 20 L6).
*Disease resistance.*—Susceptible to powdery mildew, and fungicides were applied to the grapevines under evaluation to control powdery mildew.
*Insect resistance.*—Insecticides were applied to the grapevines under evaulation to control grapevine leafhoppers and variegated leafhoppers. No resistances to these pests were determined in these evaluations due to chemical control of these pests.

LEAVES

Size:
*Generally.*—Leaves simple and alternate. The mid vein (L1) is 14.2 cm long, vein L2 is 11.1 cm long and vein L3 is 7.8 cm long. The angle between the mid vein L1 and L3 is 106 degrees and between L1 and the 1st vein off L3 is 165 degrees.
*Average length.*—19.5 cm.
*Average width.*—17.5 cm.
*Shape.*—Orbicular
*Lobes.*—Number — Five (5).
*Color.*—Upwardly Disposed Surface — Dark green (plate 23 L12). Upward surface is glabrous, flat and smooth to bullate.
*Color.*—Downwardly Disposed Surface — Green (plate 22 K9). Lower surface is glabrous with very few short hairs along the main midrib vein.
*Color.*—Leaf Vein — Light green (plate 19 I5) with occasional red (plate 6 I4) on main veins near center of leaf.
*Leaf vein.*—Thickness — Thickness of mid vein at center of leaf is 1.5 mm.
*Main veins.*—Anthocycanin — Location — With occasional red (plate 6 I4) on main veins near center of leaf.
*Leaf margin.*—Serrated with shape of teeth pointed and medium in size.
*Petiole sinus.*—Lyre shape and usually petiole lobes are half overlapped causing a closed petiole sinus. On mature leaf is 3.4 cm deep and 1.2 cm wide at widest point.
*Petiole.*—Size — Medium.
*Petiole.*—Length — 11.5 cm.
*Petiole.*—Diameter — 2.8 mm.
*Petiole.*—Color — Yellow green (plate 20 L7) with 50% red (plate 45 J3) covering. Young leaf — Upper Surface — Color — Green (plate 22 L7) with very light cobwebby indument on upper surface.
*Young leaf.*—Lower Surface — Color — Pale green (plate 21 L8).
*Young leaf.*—Shape unfolded — Concave to flat.
*Petiole of young leaf.*—Color — Green (plate 20 L7).
*Stipules.*—Onion skin.

TRUNK

*Size.*—Large.
*Size.*—Height — Approximately 104 cm above the vineyard floor.
*Size.—Diameter.*—6.47 cm as measured just below the cordon or head point at 81.28 cm above vineyard floor; and 6.63 cm at 15.2 cm above the vineyard floor.
*Bark.*—Color — (plate 16 C7).

FLOWERS

*Flower.*—Size — Generally — Medium.
*Flower.*—Unopened — Diameter — 2.1 mm.
*Flower.*—Unopened — Length — 2.9 mm.
*Flower.*—Unopened — Surface Texture — Smooth.
*Date of bloom.*—First bloom May 7, 2002.
*Date of full bloom.*—May 16, 2002 at 90%.
*Inflorescence.*—Panicle.
*Cluster size.*—At Bloom — Generally, medium.
*Cluster.*—Length — 17.0 cm.
*Cluster.*—Width — 11.0 cm.
*Peduncle.*—Length — 3.9 cm.
*Shape of cluster.*—Conical with short shoulders.
*Calyptra.*—Color — Green (plate 20 J7).
*Stamens.*—Five (5) and erect.
*Pistil.*—Well developed.
*Ovary.*—Color — Dark green (plate 22 L9).
*Pollen.*—Normal, fertile, abundant.
*Anthers.*—Color — Light yellow (plate 10 J1).

FRUIT

Maturity when described: Ripe for commercial harvesting and shipment approximately October 23 in Fresno, Calif. Late season or 8 weeks after 'Thompson Seedless' grapevine or 4 weeks after 'Autumn Seedless' grapevine.

Cluster:
*Size.* —Cane Pruned Vines — 539 grams.
*Length.*—28.5 cm.
*Width.*—16.3 cm.
*Shape.*—Conical to cylindrical.
*Density.*—Medium to tight, on average has 55 berries per cluster.
*Clusters per vine.*—56, cane pruned.
*Clusters per shoot.*—1.02 clusters per shoot.

Peduncle:
*Size.*—Length — Medium, 5.0 cm.
*Size.*—Diameter — Medium, 6.0 mm.
*Color.*—Green (plate 21 L7).
*Texture.*—Smooth, glabrous.

Pedicel:
*Generally.*—There is a medium to good attachment between the berry and the pedicel.
*Size.*—Length — 8.1 mm.
*Size.*—Diameter — 1.6 mm.
*Color.*—Green (plate 21 I5).
*Texture.*—Glabrous with a few lenticels.
*Brush.*—Length — 2.8 mm.
*Brush color.*—Green (plate 19 F1).

Berry:
*Size.*—Large, avg. 9.8 grams.
*Shape.*—Cylindrical to ovoid.
*Length.*—3.1 cm.
*Width.*—2.3 cm.
*Color.*—Pale green (plate 19 E1).
*Bloom.*—Light.
*Skin: Generally.*—The skin adheres to the flesh.
*Thickness.*—Medium in thickness.
*Texture.*—Smooth.
*Tendency to crack.*—None.

Flesh:
*Flesh color.*—Translucent and very pale yellow green (plate 19 I1).
*Texture.*—Firm, meaty.
*Juice production.*—Medium.
*Color of juice.*—Clear.
*Flavor.*—Sweet and sub acid, neutral flavor.
*Soluble solids.*—18.6%.
*Titratable acid.*—0.31 g/100 ml juice.
*Aroma.*—None.
*Ripening.*—Uniform.
*Eating quality.*—Very good, sweet.

Character of seeds: Stenospermocarpic seedless, small aborted seed traces that are not noticeable when eaten. Average aborted seed trace when present are 6.4 mg fresh weight, 3.8 mm long and 1.8 mm wide. Seed color is light brown (plate 13 C8).

Use: Fresh market. No wine nor raisin evaluations have been done.

Keeping quality: Very good.

Resistance to disease: No resistance to powdery mildew.

Shipping and handling qualities: Berries ship and handle similar to 'Thompson Seedless' except there is less berry shatter.

Although the new variety of grapevine possesses the described characteristics noted above as a result of the growing conditions prevailing in Fresno, Calif. in the central San Joaquin Valley of California, United States of America, it is to be understood that variations of the usual magnitude and characteristics incident to changes in growing conditions, training, irrigation, fertilization, pruning, pest control, climatic variation and the like are to be expected.

Having thus described and illustrated our new variety of grapevine, what we claim as new and desire to be secured by Plant Letters Patent is:

1. A new and distinct variety of grapevine plant, 'Autumn King', substantially as illustrated and described, characterized by its attractive pale green fruit color, cylindrical to ovoid fruit shape, and firm flesh texture with a neutral sweet flavor.

* * * * *